United States Patent

Bergfeld et al.

[11] Patent Number: 6,166,232
[45] Date of Patent: Dec. 26, 2000

[54] PROCESS FOR PRODUCING ESTER QUATS

[75] Inventors: Manfred Bergfeld, Erlenbach-Mechenhard; Hartmut Ahrens, Kleinwallstadt; Axel Carstens, Aschaffenburg, all of Germany

[73] Assignee: Akzo Nobel NV, Arnhem, Netherlands

[21] Appl. No.: 09/180,942

[22] PCT Filed: Jun. 6, 1997

[86] PCT No.: PCT/EP97/02941

§ 371 Date: Dec. 8, 1998

§ 102(e) Date: Dec. 8, 1998

[87] PCT Pub. No.: WO97/47588

PCT Pub. Date: Dec. 18, 1997

[30] Foreign Application Priority Data

Jun. 12, 1996 [DE] Germany .................. 196 23 325

[51] Int. Cl.$^7$ .................................................. C07F 9/02
[52] U.S. Cl. ........................... 554/84; 554/63; 554/109; 554/110; 159/49; 203/34
[58] Field of Search ................. 554/84, 63, 109; 554/110; 159/49; 203/34

[56] References Cited

U.S. PATENT DOCUMENTS

| | | | |
|---|---|---|---|
| 2,173,058 | 9/1939 | Kritchevsky | 554/63 |
| 2,228,985 | 1/1941 | Groote et al. | 554/109 |
| 4,197,350 | 4/1980 | Kleber et al. | 428/392 |
| 4,456,554 | 6/1984 | Walz et al. | 554/84 |
| 4,830,771 | 5/1989 | Ruback et al. | 252/8.63 |
| 5,190,618 | 3/1993 | Top et al. | 203/34 |
| 5,750,492 | 5/1998 | Contet et al. | 510/527 |

OTHER PUBLICATIONS

Methoden der organischen Chemie (Houben–Weyl) 1958, Stickstoff–Verbindungen II und III, p. 631.
Suo, Fuxi et al., "Synthesis and antistatic effect of quaternary ammonium salts of fatty ester," Huadong Huagong Xueyuan Xuebao, 1993, 19(5), pp. 594–599.(Abstract only).
Komkov, I.P. et al., "Surface–active quaternary ammonium salts of 0–acylcholines," Izv. Vyssh. Ucheb. Zaved., Khim. Khim. Tekhnol., 1971, 14(9), pp. 1369–1373. (Abstract only).
Vorona, N. I. et al., "Synthesis of surface–active acylcholine chlorides," Izv. Vyssh. Ucheb. Zaved., Khim. Khim. Tekhnol., 1977, 20(8), pp. 1243–1245.(Abstract only).

*Primary Examiner*—Paul J. Killos
*Assistant Examiner*—Taylor Oh
*Attorney, Agent, or Firm*—Oliff & Berridge, PLC

[57] ABSTRACT

A process is described for producing ester quats of the formula (I)

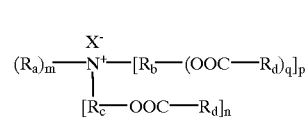

where $X^-$ is an anion of an inorganic or organic acid, $R_a$ is a $C_1$ to $C_4$ alkyl group, $R_b$ and $R_c$ are each, independently of one another, a $C_1$ to $C_3$ alkylene group, and $R_d$ is a $C_1$ to $C_{22}$ fragment of a saturated and/or unsaturated aliphatic carboxylic acid, m, n, p, and q are integers, m has a value from 1 to 3, n a value from 0 to 3, p a value from 0 to 1, m+n+p=4, and q has the value 1 or, if m=3, n=0, and p=1, the value 2, in which process a quaternary compound of the formula (II)

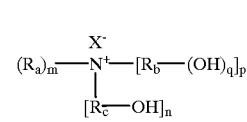

where $X^-$, $R_a$, $R_b$, $R_c$, m, n, p, and q have the above meanings, is esterified, in the presence of an oxo acid of phosphorus and/or one of its alkali or alkaline-earth salts as a catalyst, with a saturated and/or unsaturated $C_1$ to $C_{22}$ carboxylic acid, alone or in a mixture, while withdrawing water.

16 Claims, No Drawings

PROCESS FOR PRODUCING ESTER QUATS

DESCRIPTION

The invention relates to a process for producing ester quats by direct esterification of quaternary ammonium salts with fatty acids.

Ester quats are quaternary ammonium compounds that are present as salts and, in addition to the quaternary ammonium function, exhibit an ester function.

Quaternary ammonium salts react readily under transfer of alkyl groups or under Hofmann elimination. Frequently, both reactions are observed in parallel. For Hofmann elimination, a base is required, and for dealkylation a nucleophile. Suitable as the base or nucleophile are the hydroxide ion and halogenide ions, among others. In the conversion of quaternary ammonium compounds with carboxylates as well, an O alkylation of the carboxylate is accompanied by the corresponding dealkylation of the ammonium component. Depending on the reaction partner, either the dealkylation or the elimination dominates (Hanhart and Ingold, *J. Chem. Soc.*, 1927, 997, V. Meyer, M. Lecco, *Liebigs Ann.* 180, 184 (1876). W. Lossen, *Liebigs Ann.* 181, 377 (1876). J. A. Zoltewicz, L. W. Deady, *Adv. Heterocycl. Chem.* 22, 71 (1978). Lawson, Collie, *J. Chem. Soc.*, 53, 624 (1888)).

For the same reason, quaternary ammonium salts are stable as phase transfer catalysts only up to temperatures of 100–150° C. (D. Landini, A. Maia, A. Rampoldi, *J. Org. Chem.* 1986, 51, 3187–3191).

Choline chloride also exhibits these properties typical of quaternary ammonium compounds. When heated, it breaks down into (dimethylamino)ethanol and methyl chloride (Ullmann's Encyclopedia of Industrial Chemistry, 5th Ed., 1986, Vol. A7, 39) and, via Hofmann elimination, releases ethene (B. A. Kurchii, *Fiziol. Biokhim. Kul't. Rast.* 1991, 23(1), 17–23, from: *Chemical Abstracts* 1991; Vol. 114, 223451w).

The Russian Journal of Applied Chemistry, Vol. 67, No. 5, Part 2, 1994, 734–736, describes the Hofmann elimination of choline ester quats.

Consequently, in the direct esterification of choline chloride with fatty acids, both the Hofmann elimination to trimethylamine and ethene and further to the vinyl ester of the corresponding fatty acid, as well as a dealkylation to (dimethylamino)ethanol and further to the (dimethylamino) ethyl ester of the corresponding fatty acid and to methyl chloride and fatty-acid methyl ester can be expected. Moreover, the quaternary ammonium group exercises a -I effect on the hydroxyl function so that the latter is inactivated for esterification (Methoden der organischen Chemie (Houben-Weyl) 1958, Stickstoff-Verbindungen II und III, 631).

For these reasons, industrial synthesis of a choline ester is not performed via direct esterification of choline chloride with the corresponding carboxylic acid. Rather, in a two-stage synthesis, (dimethylamino)ethanol is first converted with the corresponding acid, and the ester is then quaternized with methyl chloride or dimethyl sulfate (Huadong Huagong Xueyuan Xuebao (1993), 19(5), 594–9). These quaternization reagents are highly toxic and also lead to methylation of the solvent.

A single-stage synthesis is described in Izv. Vyssh. Ucheb. Zaved., *Khim. Khim. Tekhnol.* (1971), 14(9), 1369–73, whereby choline chloride is converted with fatty-acid chlorides. Acid chlorides, however, must have previously been produced from the free acids, so that the raw-material price is significantly higher. Moreover, they are corrosive, sensitive to moisture, and difficult to handle due to their high reactivity, so that they can be used industrially only at considerable expense. As a result, such choline ester quat synthesis is not economical.

Likewise uneconomical is the transformation of fatty-acid (2-chloroethyl) ester with trimethylamine, since the ester must be produced prior to quaternization (Izv. Vyssh. Uchebn. Zaved., *Khim. Khim. Tekhnol.* (1977), 20(8), 1243–5).

Compounds of this type are also described, for example, in WO 91/01295. According to the process described therein, an esterification of a fatty acid with an alkanolamine is first conducted, and the ester obtained is quaternized with substances such as dimethyl sulfate or methyl chloride in solvents such as isopropyl alcohol. One disadvantage in such processes, among other things, is that toxic substances such as dimethyl sulfate or methyl chloride are used. A further disadvantage of such processes is that the solvent can be methylated in the second stage, for example isopropyl alcohol to isopropyl methyl ether.

The need therefore exists for an improved process for producing ester quats in which the aforementioned disadvantages do not arise.

The object of the invention is therefore to provide a process for producing ester quats that works without such highly toxic substances as dimethyl sulfate or methyl chloride, can be conducted in a single stage, is based on inexpensive starting materials, and results in ester quats of high purity, i.e., which exhibit no or only a small amount of byproducts such as ester amines or fatty-acid methyl esters and, in addition to the main product, also possibly contain a fraction of free fatty acid.

This object is met by a process for producing ester quats with the formula (I)

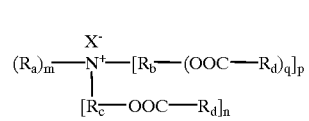

(I)

where $X^-$ is an anion of an inorganic or organic acid, $R_a$ is a $C_1$ to $C_4$ alkyl group, $R_b$ and $R_c$ are each, independently of one another, a $C_1$ to $C_3$ alkylene group, and $R_d$ is a $C_1$ to $C_{22}$ fragment of a saturated and/or unsaturated aliphatic carboxylic acid, m, n, p, and q are integers, m has a value from 1 to 3, n a value from 0 to 3, p a value from 0 to 1, m+n+p=4, and q has the value 1 or, if m=3, n=0, and p=1, the value 2, characterized in that a quaternary compound of the formula (II)

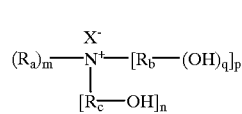

(II)

where $X^-$, $R_a$, $R_b$, $R_c$, m, n, p, and q have the above meanings, is esterified, in the presence of an oxo acid of phosphorus and/or one of its alkali or alkaline-earth salts as a catalyst, with a saturated and/or unsaturated $C_1$ to $C_{22}$ carboxylic acid, alone or in a mixture, while withdrawing water, and the reaction mixture thus produced possibly undergoes further processing.

The carboxylic acid is preferably a fatty acid with 6 to 22 carbon atoms.

The water produced during esterification must be removed to increase the conversion efficiency, for example in a vacuum or by using an appropriate water trap.

The process is preferably performed in a vacuum of $p \leq 200$ mbar.

Oxo acids of phosphorus are used as catalysts, for example diphosphoric acid, metaphosphoric acid, polyphosphoric acid, in particular phosphoric acid, phosphorous acid, and hypophosphorous acid or their salts such as $Na_3PO_4 \cdot 10H_2O$, monosodium dihydrogen hypophosphite, and sodium hypophosphite monohydrate. The catalysts can be either in substance form or in solutions, whereby aqueous solutions are preferred.

It is advantageous to conduct the esterification with an excess of carboxylic acid, the excess being selectable within a wide latitude. Advantageously, at least 1.5 mol, especially preferably 4–20 mol, of carboxylic acid is used per mole of choline salt.

The temperature is advantageously at least 100° C., whereby the range 130 to 220° C. is preferred and the range 150 to 170° C. is especially preferred.

The esterification can be conducted advantageously in a reactor having a water trap.

Further processing of the resulting reaction mixture can be advantageously performed with a film evaporator. In this processing, at least a portion of the excess carboxylic acid is separated off, for which a film evaporator is especially suitable.

Quaternary compounds of formula (II), for example choline chloride, are used as the starting substance for esterification. Choline chloride can be produced in a simple manner from trimethylamine, ethylene oxide, carbon dioxide, and water, whereby choline hydrogen carbonate is initially produced, which is then transformed to the corresponding choline chloride on acidification with hydrochloric acid.

Other suitable choline salts are described in the French patent specification 736 107, among others.

For esterification, conventional carboxylic acids from natural sources can be used, or they can also be produced synthetically. Carboxylic acid mixtures can also be used, including those containing saturated alkane acids and acids with one or more double bonds. The use of fatty acids with 6 to 22 carbon atoms and mixtures thereof is preferred.

After conclusion of esterification, the reaction mixture obtained is preferably processed further, i.e., excess carboxylic acid can be separated off, for example. This is performed preferably by distillation, whereby film distillation is particularly suited. This results in an ester quat residue of high purity, which, depending on the distillation conditions, can also contain a portion of excess carboxylic acid and also the catalyst.

Generally speaking, any residual catalyst can remain in the product. It can, however, also be converted to neutral salts.

It was especially surprising that it was possible using the process of the invention to obtain ester quats through direct esterification of quaternary compounds of formula (II), since the hydroxyl function is inactivated for esterification as a result of the ammonium group, and the aforementioned breakdown reactions were expected instead of esterification.

Furthermore, it is not essential to conduct the complicated multi-stage prior-art processes, which moreover require the use of toxic substances. The conversion efficiency of the quaternary compound of formula (II) is very high, with a selectivity that is high for ester quats. The conversion efficiency, with respect to the choline salt used, generally exceeds 92%. The occurrence of byproducts is slight. Residual fractions can in general be completely removed when the carboxylic acid is also removed by distillation.

The process is readily manageable on an industrial scale. The catalysts employed can generally remain in the final product.

The excess carboxylic acid used in esterification can easily be recovered and used again in the process.

The invention will be explained in more detail on the basis of the following examples:

EXAMPLE 1

In a three-necked flask with water trap, 1163.9 g (5.62 mol) cocinic acid and 112 g (96%; 0.77 mol) choline chloride were heated to 160° C. while adding 4 ml (50%; 0.04 mol) hypophosphorous acid. Under a vacuum of 6 mbar, the reaction mixture was stirred for 4 hours at this temperature. Subsequently, a large portion of the unconverted fatty acid was distilled off on a film evaporator. 191.5 g of a light-colored solid was isolated, with the following composition:

| | |
|---|---|
| Choline ester quat | 59.7% by weight |
| Choline chloride | 0.3% by weight |
| Free fatty acid | 38.6% by weight |
| Hypophosphorous acid | 1.3% by weight |

The conversion efficiency of choline chloride resulting from these figures is 99.5%.

EXAMPLE 2

In a three-necked flask with water trap, 32.03 g (0.16 mol) lauric acid and 3.89 g (75%; 20.0 mmol) of an aqueous choline chloride solution were heated to 160° C. while adding 0.1 ml (85%; 1.5 mmol) phosphoric acid. Under a vacuum that developed within one hour from 39 mbar to 10 mbar, the reaction mixture was stirred for 4 hours at this temperature. A conversion efficiency of 96.4% with respect to choline chloride was attained. The selectivity of the conversion to choline ester quat was 88.5%, and the yield of choline ester quat was 85.3%.

EXAMPLE 3

In a three-necked flask with water trap, 20.0 g (0.10 mol) lauric acid and 2.9 g (96%; 20.0 mmol) choline chloride were heated to 160° C. while adding 0.5 ml (50%; 4.8 mmol) of an aqueous solution of hypophosphorous acid. Under a vacuum that developed within one hour from 39 mbar to 10 mbar, the reaction mixture was stirred for 4 hours at this temperature. A conversion efficiency of 96.9% with respect to choline chloride was attained. The selectivity of the conversion to choline ester quat was 96.5%, and the yield of choline ester quat was 93.5%.

EXAMPLE 4

In a Büchi autoclave with base drain and condenser, 465.6 g (2.24 mol) cocinic acid was mixed with 8 ml (50%, 0.08 mol) hypophosphorous acid and heated to 150° C. Within one hour, a total of 57.2 g (75%, 0.31 mol) of an aqueous solution of choline chloride was added using a peristaltic pump, at 150° C. and a vacuum of 20 mbar. Subsequently, the reaction mixture was stirred for an additional 5 hours under a vacuum of 6 mbar at this temperature. Finally, the content was cooled to 100° C., and the autoclave was ventilated. The product was drained off. A conversion efficiency of 99.3% with respect to choline chloride was attained. The selectivity of the conversion to choline ester quat was 94.2%, and the yield of choline ester quat was 93.5%.

EXAMPLE 5

In a three-necked flask with water trap, 60.4 g (0.30 mol) lauric acid and 2.8 g (96%; 19.3 mmol) of choline chloride were heated to 160° C. while adding 0.23 g (0.61 mmol) trisodium phosphate dodecahydrate. Under a vacuum of 150 mbar, the reaction mixture was stirred for 4 hours at the aforementioned temperature. A conversion of 93% with respect to choline chloride was attained. The selectivity of the conversion to choline ester quat was 85.6%, and the yield of choline ester quat was 79.7%.

EXAMPLE 6

In a three-necked flask with water trap, 60.3 g (0.30 mol) lauric acid and 2.9 g (96%; 20.0 mmol) of choline chloride were heated to 160° C. while adding 0.13 g (0.61 mmol) of monosodium dihydrogen hypophosphite. Under a vacuum of 150 mbar, the reaction mixture was stirred for 4 hours at the aforementioned temperature. A conversion efficiency of 92.5% with respect to choline chloride was attained. The selectivity of the conversion to choline ester quat was 85.7%, with a yield of choline ester quat of 79.2%.

EXAMPLE 7

In a three-necked flask with water trap, 20.2 g (100 mmol) Kortacid C70 and 3.8 g (10 mmol) ACER 96S038 were heated to 150° C. while adding 0.5 g (5 mmol) sodium hypophosphite monohydrate. Kortacid C70 is a mixture of fatty acids of the structure R'—COOH, where R' stands for $C_8H_{15}$, $C_{10}H_{21}$, $C_{12}H_{23}$, $C_{14}H_{25}$, and $C_{16}H_{27}$. ACER 96S038 is a mixture of diols of formulas (2a), (2b), and (2c)

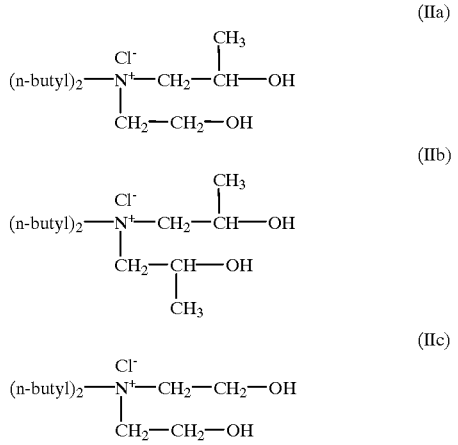

with a molar ratio of the 2-hydroxyethyl to the 2-hydroxypropyl groups of 9:1. Under a vacuum that developed within one hour from 40 to 10 mbar, the reaction mixture was stirred for 6 hours at 150° C. According to the results of $^1H$ NMR spectroscopy, 94% of the hydroxyl groups had been esterified.

EXAMPLE 8

Example 7 was repeated, except that 1.1 g (10 mmol) sodium hypophosphite monohydrate was used. According to the results of $^1H$ NMR spectroscopy, 96% of the hydroxyl groups had been esterified.

EXAMPLE 9

In a three-necked flask with water trap, 20 g (0.10 mol) lauric acid and 1.7 g (10 mmol) of dimethyl(bis-2-hydroxyethyl)ammonium chloride were heated to 150° C. while adding 0.5 ml (50%; 4.8 mmol) of an aqueous solution of hypophosphorous acid. Under a vacuum which developed within one hour from 39 to 10 mbar, the reaction mixture was stirred for 6 hours at the aforementioned temperature. A conversion of 97.6% with respect to the dimethyl(bis-2-hydroxyethyl)ammonium chloride was attained. The selectivity of the conversion to diester quat was 70%. The yield of diester quat was 68.3%.

EXAMPLE 10

Example 9 was repeated, except that 1.0 ml (50%; 9.6 mmol) of an aqueous solution of hypophosphorous acid was used. A conversion of 98.4% with respect to the dimethyl (bis-2-hydroxyethyl)ammonium chloride was attained. The selectivity of the conversion to diester quat was 79%. The yield of diester quat was 77.7%.

EXAMPLE 11

Example 9 was repeated, except that 0.5 g (5.0 mmol) of sodium hypophosphite monohydrate was used as a catalyst. A conversion of 99.9% with respect to the dimethyl(bis-2-hydroxyethyl)ammonium chloride was attained. The selectivity of the conversion to diester quat was 83.4%. The yield of diester quat was 83.3%.

EXAMPLE 12

Example 11 was repeated, except that 1.1 g (10.0 mmol) of sodium hypophosphite monohydrate was used as a catalyst. A conversion of 98.5% with respect to the dimethyl (bis-2-hydroxyethyl)ammonium chloride was attained. The selectivity of the conversion to diester quat was 89.7%. The yield of diester quat was 88.4%.

EXAMPLE 13

In a three-necked flask with water trap, 20.0 g (0.10 mol) lauric acid and 1.7 g (10,0 mmol) of 2,3-dihydroxypropyltrimethylammonium chloride were heated to 150° C. while adding 1 ml (50%; 9.6 mmol) of an aqueous solution of hypophosphorous acid. Under a vacuum which developed within one hour from 39 to 10 mbar, the reaction mixture was stirred for 8 hours at the aforementioned temperature. A conversion of 96.5% with respect to the 2,3-dihydroxypropyltrimethylammonium chloride was attained. The selectivity of the conversion to diester quat was 71.5%. The yield of diester quat was 69.0%.

EXAMPLE 14

In a three-necked flask with water trap, 20.0 g (0.10 mol) lauric acid and 1.6 g (10 mmol) of tris(2-hydroxyethyl) methylammonium chloride were heated to 145° C. while adding 1.1 g (10 mmol) of sodium hypophosphite monohydrate. Under a vacuum which developed within one hour from 40 to 10 mbar, the reaction mixture was stirred for 3 hours at the aforementioned temperature. A conversion of 70.9% with respect to the tris(2-hydroxyethyl) methylammonium chloride was attained. The selectivity of the conversion to diester quat was 95.1%. The yield of triester quat was 67.4%.

EXAMPLE 15

Example 14 was repeated, except that the reaction mixture was stirred for 4 hours. The yield of triester quat was 75.0%.

What is claimed is:

1. Process for producing ester quats with the formula (I)

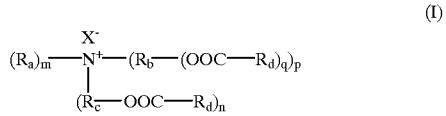

(I)

where $X^-$ is an anion of an inorganic or organic acid, $R_a$ is a $C_1$ to $C_4$ alkyl group, $R_b$ and $R_c$ are each, independently of one another, a $C_1$ to $C_3$ alkylene group, and $R_d$ is a $C_6$ to $C_{22}$ fragment of a saturated or unsaturated aliphatic carboxylic acid, m, n, p, and q are integers, m has a value from 1 to 3, n a value from 0 to 3, p a value from 0 to 1, m+n+p=4, and q has the value 1 or, if m=3, n=0, and p=1, the value 2, the process comprising esterifying a quaternary compound of the formula (II)

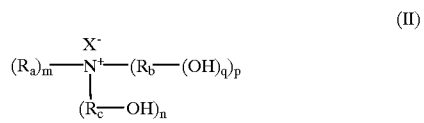

(II)

where X, $R_a$, $R_b$, $R_c$, m, n, p, and q have the above meanings, in the presence of a catalyst comprising at least one of an oxo acid of phosphorus, an alkali salt of an oxo acid of phosphorus, an alkaline-earth salt of an oxo acid of phosphorus, or mixtures thereof, with a saturated or unsaturated aliphatic $C_6$ to $C_{22}$ carboxylic acid, alone or in a mixture, while withdrawing water.

2. Process in accordance with claim 1, characterized in that water is continually removed during esterification.

3. Process in accordance with claim 1 or 2, characterized in that the water is removed by vacuum.

4. Process in accordance with one of claims 1 to 3, characterized in that the esterification is conducted at a pressure $p \leqq 200$ mbar.

5. Process in accordance with one of claims 1 to 4, characterized in that phosphoric acid is used as the oxo acid of phosphorus.

6. Process in accordance with one of claims 1 to 4, characterized in that phosphorous acid is used as the oxo acid of phosphorus.

7. Process in accordance with one of claims 1 to 4, characterized in that hypophosphorous acid is used as the oxo acid of phosphorus.

8. Process in accordance with claim 1, wherein the alkali salt of an oxo acid of phosphorous is selected from $Na_3PO_4 \cdot 10H_2O$, monosodium dihydrogen hypophosphite, and sodium hypophosphite monohydrate.

9. Process in accordance with one of claims 1 to 8, characterized in that an excess of carboxylic acid is used for esterification of the quaternary compound of formula (II).

10. Process in accordance with claim 9 wherein at least 1.5 mol of carboxylic acid is used per mole of quaternary compound of formula (II).

11. Process in accordance with one of claims 1 to 10, characterized in that the esterification is conducted at an elevated temperature of at least 100° C.

12. Process in accordance with claim 11, characterized in that the temperature is 130 to 220° C.

13. Process in accordance with claim 12, characterized in that the temperature is 150 to 170° C.

14. Process in accordance with one of claims 1 to 13, characterized in that the esterification is conducted in a reaction vessel with water separator.

15. Process in accordance with one of claims 1 to 14, characterized in that existing excess carboxylic acid and byproducts are completely or partially separated from the resulting ester quat using a film evaporator.

16. Process in accordance with claim 1, wherein 4–20 mol of carboxylic acid is used per mole of quaternary compound of formula (II).

* * * * *

UNITED STATES PATENT AND TRADEMARK OFFICE
CERTIFICATE OF CORRECTION

PATENT NO. : 6,166,232  
DATED : December 26, 2000  
INVENTOR(S) : Manfred Bergfeld and Hartmut Ahrens Page 1 of 2

It is certified that error appears in the above-identified patent and that said Letters Patent is hereby corrected as shown below:

<u>Title page,</u>
Item [56] References Cited, please add the following:

FOREIGN PATENT DOCUMENTS

| | | |
|---|---|---|
| WP91/01295 | 02/1991 | WIPO |
| 736,107 | 11/1932 | FRANCE |
| JP-A-6-279371 | 10/1994 | JAPAN |
| DE 4409322C1 | 04/1995 | GERMANY |

OTHER PUBLICATIONS

Hanhart, Walther, et al., "The Nature of the Alternating Effect in Carbon Chains. Part XVIII. Mechanism of ExHausive Methylation and its Relation to Anomalous Hydrolysis", February 1927, The University, Leeds, pp. 997-1020.

Meyer, Victor, et al. "Untersuchungen ubder die Constitution der Ammoniumverbindungen und des Salmiaks", Liebigs Ann. 180 (1876), pp.173-191.

Lossen, W. "Ueber Ammoniumverbindungen", Liebigs Ann. (1876), pp. 364-383.

Zoltewicz, John A., et al., "Quaternization of Heteroaromatic Compounds: Quantitative Aspects", Adv. Heterocycl. Chem 22, (1978), pp. 71-121.

Lawson, A.T., et al. "The Action of Heat on the Salts of Tetramethylammonium", J. Chem. Soc., 53 (1888), pp. 624-636.

Landini, Dario, et al. "Stability of Quaternary Onium Salts under Phase-Transfer Conditions in the Presence of Aqueous Alkaline Solutions", J. Org.Chem., Vol. 51, No. 16, 1986, pp. 3187-3191.

Suzuki, Yoshihisa. "Choline", Allmann's Encyclopedia Of Industrial Chemistry, 5$^{th}$ Ed., 1986, Vol. A7, pp. 39-41.

Kurchii, B.A., "Ethylene Formation from Quaternary Ammonium Salts by Hofman Degradation", Fiziol. Biokhim. Kul't Rast., Chemical Abstracts Vol. 114, 1991, No. 223451w.

UNITED STATES PATENT AND TRADEMARK OFFICE
CERTIFICATE OF CORRECTION

PATENT NO. : 6,166,232
DATED : December 26, 2000
INVENTOR(S) : Manfred Bergfeld and Hartmut Ahrens It is certified that error appears in the above-identified patent and that said Letters Patent is hereby corrected as shown below:

Ryzhkov, Yu, A., et al. "Synthesis and Thermal Stability of cationic Surface-Active Dimethylaminoethanol Derivatives", Russian Journal of Applied Chemistry, Vol. 67, No. 5, Part 2, 1994, 734-736.

Takayanagi, Yasuyuki, et al. "Manufacture of Unsaturated Quaternary Ammonium Salts", Jpn. Kokai Tokkyo Koho JP 06,279,371, Chemical Abstracts, Vol. 122, 1995, No. 186940x.

Column 6,
Line 67, "triester" should be "diester".

Column 7,
Line 38, "claim 1 or 2" should be "claim 1".

Column 8,
Lines 1, 4, 8, "one of claims 1 to 4" should be "claim 1".
Line 15, "one of claims 1 to 8" should be "claim 1".
Line 22, "one of claims 1 to 10" should be "claim 1".
Line 30, "one of claims 1 to 13" should be "claim 1".
Line 33, "one of claims 1 to 14" should be "claim 1".

Signed and Sealed this

Fourteenth Day of August, 2001

*Attest:*

NICHOLAS P. GODICI
*Attesting Officer*  Acting Director of the United States Patent and Trademark Office